United States Patent [19]

Eda

[11] Patent Number: 4,504,466

[45] Date of Patent: Mar. 12, 1985

[54] PERMANENT HAIR-WAVING

[76] Inventor: Tadaji Eda, 1-16A-208, Meguro 1 chome, Meguro-ku, Tokyo 153, Japan

[21] Appl. No.: 167,358

[22] Filed: Jul. 10, 1980

[51] Int. Cl.$^3$ .................. A61K 7/09; A45D 19/00
[52] U.S. Cl. ............................................ 424/72; 132/7
[58] Field of Search ............................... 424/72; 132/7

[56] References Cited

U.S. PATENT DOCUMENTS

| 2,466,963 | 4/1949 | Patrick et al. ............... 260/79.1 |
| 2,841,530 | 7/1958 | Andersen et al. ................ 424/72 |
| 4,192,863 | 3/1980 | Kondo ............................ 424/72 |

FOREIGN PATENT DOCUMENTS

| 1198491 | 8/1965 | Fed. Rep. of Germany ........ 424/72 |
| 2141763 | 3/1973 | Fed. Rep. of Germany ........ 424/72 |
| 2822125 | 11/1979 | Fed. Rep. of Germany ........ 424/72 |
| 1003963 | 11/1951 | France .......................... 424/72 |
| 448052 | 5/1949 | Italy ............................ 424/72 |
| 1119845 | 7/1968 | United Kingdom ................ 424/72 |

OTHER PUBLICATIONS

Jorczak et al., Industrial & Engineering Chem., 10/1950, vol. 43, No. 2, pp. 324–328.

*Primary Examiner*—Dale R. Ore
*Attorney, Agent, or Firm*—Richard P. Crowley

[57] ABSTRACT

A novel permanent hair-waving solution comprising as its main ingredient a sulfide, hydrosulfide or mercaptan compound and an air oxidation accelerator characterized by further containing a sulfite compound, the molar ratio of the sulfite to the sulfide, hydrosulfide or mercaptan compound being 1.0 or more, said solution containing free alkali to give a pH of from 8 to 11 and containing also an aqueous carrier for said compounds and said alkali, which is useful to impart a permanent waving to hair in the cold.

22 Claims, No Drawings

PERMANENT HAIR-WAVING

DETAILED EXPLANATION OF THE INVENTION

The present invention relates to a novel one-step permanent hair-waving solution, and particularly to the novel one-step permanent hair-waving solution which contains no mercaptan compound such as thioglycolate as an active ingredient or contains far smaller amount of the mercaptan compound to obtain a truly non-damaged odorless hair after short operation harmlessly. More particularly, it relates to a novel one-step permanent hair-waving solution comprising as its main ingredient a sulfide, hydrosulfide or mercaptan compound and an air oxidation accelerator characterized by further containing a sulfite, the molar ratio of the sulfite to the sulfide, hydrosulfide or mercaptan compound being 1.0 or more, said solution containing free alkali to give a pH of from 8 to 11 and containing also an aqueous carrier for said compounds and said alkali, which is useful to impart a permanent waving to hair in the cold. Further, the present invention relates to a process of giving permanent waving shape to hair by using the said permanent hair-waving solution.

The permanent hair-waving solutions now widely employed in the world are classified into the following two main groups in respect of the application method, as already described in U.S. Pat. No. 4,192,863 and the like.

(1) Two-step Permanent Hair-waving Solution

This solution is widely employed in professional beauty parlors and the application method comprises tightly winding on about 60 rods or curlers having diameters of about 2 to 10 mm, hair which is coated with a first solution practically containing 5 to 8% by weight of alkali thioglycolate or a modification thereof as a main component. This winding operation takes about 20 minutes. Then the wound hair is again coated with the said solution and a vinyl cap is placed on the head of the user for about 10 to 30 minutes until the solution dissolves and softens the hair surface. Then a second solution containing about .2 to 6% by weight of a strong oxidizing agent such as potassium bromate, sodium bromate, hydrogen peroxide or the like, or oxygen gas is applied to the hair for about 20 to 30 minutes to fix and deodorize the dissolved and softened hair. The hair is then unwound from the rods or curlers and subjected to a warm-rinse for about 5 to 10 minutes. The hair is then coated with a hair setting lotion and wound on 30 to 60 curlers having diameter of 1 to 3 cm to produce large curls of 2 to 6 cm in diameter according to preference. This takes about 20 minutes. The hair is then dried with hot air at a temperature of about 45° C. for about 25 minutes, after which the hair is unwound from the curlers, and brushed and arranged with a comb and hairpins to complete the hair-dressing.

(2) One-step Permanent Hair-waving Solution

This solution comprises almost the same composition as that of the above-mentioned first solution which dissolves and softens the hair, and then fix the hair by means of air oxidation, but the application method thereof in professional beauty parlors employs the above-mentioned second solution to remove the bad smell of hydrogen sulfide and the like produced by the decomposition of the thioglycolate when applied. Otherwise, the bad smell cannot be removed at one time and it becomes necessary to fully water-rinse the hair and to subject the hair to natural deodorization in air for about four weeks. Accordingly, the conventional one-step permanent hair-waving solutions are not true one-step ones but actually belong to the two-step solutions.

As seen from the above, the conventional two-step or one-step solution takes at least 120 minutes to complete the permanent hair-waving and such a long application period represents a troublesome drawback.

Furthermore, the conventional permanent hair-waving solutions generally contain 1 to 10% by weight of thioglycollic acid for dissolving and softening the hair whereby cystine and by-product systeine contained in the hair dissolve out and react with heating or with strong oxidizing agent to produce hydrogen cyanide and other cyano compounds as pollutants which can effect chemical poisoning, such as pernicious anemia, cirrhosis of the liver or the like, and the thioglycollic acid retained in the hair renders the hair porous, coarse, non-sleek and discolored.

Permanent hair-waving solutions are disclosed in U.S. Pat. Nos. 3,025,218 (Strain et al), 2,631,965 (Schnell), 3,148,126 (Martin) and 4,192,863 (Kondo), and Japanese Pat. No. 299,121 (Publication No. 450/1961) (Kondo).

The U.S. Pat. No. 3,025,218 is a two-step type and employs a large amount of tartaric acid only for lowering the pH of the permanent hair-waving solution but still causing the dissolved and softened hair to have a bad smell, and accordingly, a setting agent for the oxidation is required whereby the applied hair is greatly damaged. In U.S. Pat. No. 2,631,965, 1 to 10% by weight of thioglycollic acid and a large amount of oxy-organic ammonium salt are contained in alkaline aqueous solution, the hair is discolored and a bad smell is produced, and for quick deodorization in beauty parlors, it is necessary to use an oxidizing agent for setting to remove the bad smell and accordingly, the solution is actually a two-step solution which damages the hair. In U.S. Pat. No. 3,148,126, the permanent hair-waving solution contains 1 to 15% by weight of thioglycolate and monoethanolamine, and still requires an oxidating agent (containing hydrogen peroxide and tartaric acid) for setting, heating at a high temperature of 150° to 200° F. or delivering oxygen gas under a helmet covering the scalp for quick deodorization and wave fixing. Accordingly, this permanent hair-waving solution also belongs properly to the two-step solution whereby the applied hair is greatly damaged. The permanent hair-waving solution of Japanese Pat. No. 299,121 is a one-step permanent hair-waving solution comprising 3 to 3.5% by weight of thioglycollic acid, 0.01 to 0.03% by weight of oxy-organic acid and 1 to 2% by weight of ethyl alcohol, and caustic alkali in an amount of 0.1% or less by weight is added to adjust the pH of the solution to 7.0 to 11.0, but this solution also has a bad smell and is poor in effect. In the permanent hair-waving solution of U.S. Pat. No. 4,192,863, the above content of oxy-organic acid is enriched from 0.01–0.03% to 0.1–0.4% by weight, and monoethanolamine, triethanolamine or a mixture thereof in an amount of 0.01 to 1.0% by weight and 1.0 to 10.0% by weight of ethyl alcohol are added to improve the deodorization and waving effects, but it shows insufficient effects in deodorization, elongation, tensile strength and the like, as shown in the below-mentioned comparative experimental examples.

The present inventor has repeatedly made studies and experiments of suitable chemicals for removing the above-mentioned drawbacks to obtain a new knowledge which is quite different from the conventional hair-waving theory, and completed the present invention.

That is, the conventional hair-waving theory and that of the present invention are as follows:

It has been considered that conventional permanent waving is carried out by cutting off the sulfur linking (—S—S—) of cystine having the formula, $$\begin{array}{l} S-CH_2CH(NH_2)COOH \\ | \\ S-CH_2CH(NH_2)COOH \end{array}$$

which is in keratin being a kind of protein and constituting hair, by means of hydrogen atoms contained in the first solution (a reducing agent such as thioglycollic acid) to produce cysteine (HS—CH$_2$CH(NH$_2$)COOH) which can be easily curled, and then fixing by means of oxygen atoms contained in the second solution (an oxidizing agent such as potassium bromate, etc.) or oxygen in the air, to recover the sulfur linking, as shown in the following formula:

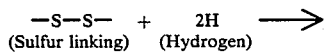

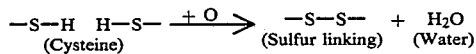

In the above case, the reducing agent of thioglycollic acid is employed in an amount of 1 to 10% by weight of the solution but when employed in an amount below 5%, it has been considered that cutting off of the sulfur linking of cystine could be possible by heating. In fact, the first solution dissolves out part of the cystine to effect softening of hair but it also causes porousness, fineness, non-sleekness and discoloration of the hair. The hair is then curled and fixed, as a common property of protein, by means of the oxidizing agent of the second solution. At the same time, the dissolved cystine or its derivatives are reacted with an excess amount of the oxidizing agent of the second solution to produce sulfurous acid compounds and cyano compounds which effect a possible chemical poisoning. Further, it is necessary to rinse the treated hair to remove the produced sulfurous acid compounds and cyano compounds and also bad smell of hydrogen sulfide or the like.

On the other hand, the permanent hair-waving of the present invention is carried out in a short time without the second solution by using a sulfide, hydrosulfide or thioglycolate and a sulfite contained in the solution to cut off the sulfur linking of the cystine in the hair as follows:

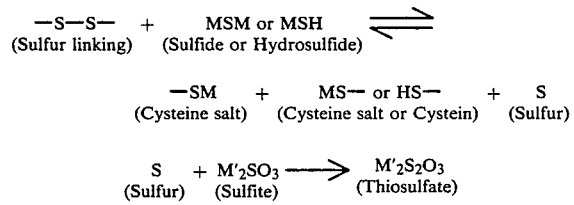

wherein M and M' are respectively an alkali metal or ammonium group, to suit the illustration's convenience.

The resulting cysteine salts and cysteines are combined to recover the sulfur linking for fixing by means of an air oxidation accelerating action of hexamethylenetetramine, iodine, bromine, iodide or bromide of alkali metal or ammonium, or mixtures thereof, as follows:

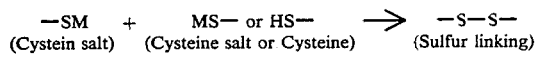

wherein M is as defined above. In this case, main content such as the sulfide, hydrosulfide or thioglycolate is far less compared with those of the conventional one-step and two-step types, the reaction immediately proceeds when applied to the hair to be treated because of the irreversible reaction, and owing to the fact that no strong oxidizing agent is not applied to the hair, the present waving solution does not generate hydrogen cyanide, etc. and neither damages the hair nor causes the porousness of the hair, while also the production cost becomes very low. The generation of bad smell of hydrogen sulfide, etc. from the sulfide or the like before the application or during the application is very little, but if necessary, it can be prevented by the adsorption with a reductive saccharide such as sucrose, glucose, fructose and the like, organic amines, lower aliphatic saturated alcohols and the like to obtain an almost odorless permanent hair-waving solution. The said reductive saccharide can also be used as an adjuvant reducing agent and an inhibiting agent of hair-dissolving action inherent to the sulfide, hydrosulfide or thioglycolate as a main ingredient of the permanent hair-waving solution of the present invention, and the said organic amines can also be used as a permeability-promoting agent into the hair.

In the next place, the flexibility and dampishness of hair are greatly influenced by moisture contained in the hair, and for the purposes of the moisture retention and prevention of a skin inflammation and a hair damage due to dissolution, the lower aliphatic saturated alcohols are contained in the permanent hair-waving solution of the present invention to utilize its affinity for water and a beauty of hair can be effected. In this case, the said alcohols can also be used as a polar solvent and a swelling agent of hair. Further, for the purpose of inhibiting the oxidation in the above-mentioned cutting off of sulfur linking of the cystine in the hair and maintaining the pH of the permanent hair-waving solution of the present invention at 8 to 11, an aliphatic oxy-organic acids such as citric acid, tartaric acid and the like must be contained, and a fatty acid ester formed by a reaction with the above-mentioned lower aliphatic saturated alcohols when simultaneously contained can carry out a cleansing action on hair as a neutral soap without destruction of tissues of skin and hair to further enhance the beautifulness of hair. Furthermore, hexamethylenetetramine, iodine, bromine, iodide or bromide of alkali metal or ammonium, or mixtures thereof must be added as an air oxidation accelerator, for accelerating the fixing of hair.

In short, the present invention can not be seen to flow from the prior art, and the unique and characteristic advantages of the present invention are as follows:

(1) The permanent hair-waving solution of the present invention provides truly elastic non-damaged, non-porous, glossy and creamy waved hair in a short time without regard to the kind and state of the hair, while the conventional permanent hair-waving solutions need an overall time of 2 hours, or more, for all processes (coating, winding, further coating, vinyl-capping, oxidizing or deodorizing, rinsing, rewinding, and drying steps) and it still causes all types of hair to be rendered porous and/or discolored.

(2) The permanent hair-waving solution of the present invention is harmless and never results in chemical poisoning with cyano compounds and the like because there is no generation of the poisonous compounds arising from the use of a strong oxidizing agent and/or neutralizing agent or from a rapid air oxidation. The conventional permanent hair-waving solutions are liable to effect chemical poisoning, such as, pernicious anemia, cirrhosis of the liver or the like due to the cyano compounds, hydrogen sulfide and the like generated in the course of the permanent waving processes.

(3) In the permanent hair-waving solution of the present invention, the content of main ingredient such as sulfide, hydrosulfide or thioglycolate is far less compared with those of the conventional one-step and two-step types, but it is most effective, harmless and substantially odorless when used, according to the above-mentioned hair waving theory of the present invention, whereas in the conventional permanent hair-waving solutions, the content of main ingredient such as thioglycolate is very large and they cause the discoloration of the hair and produce the bad smell of hydrogen sulfide and further is liable to produce poisonous cyano compounds when the oxidizing agent is applied or even when the air oxidation for fixing the hair in the conventional one-step permanent hair-waving solution is applied which can be injurious to human health in repeated applications and can damage the beauticians' finger tips, finger nails and also damage the hair in a single use to produce a rough touch and affording no gloss.

(4) Hairdyeing can be carried out in advance to provide brilliantly colored hair without discoloration due to the application of the permanent hair-waving solution of the present invention even immediately after the hair-dyeing, while the conventional permanent hair-waving solutions can not be applied immediately after the hairdyeing because the waving solutions positively dissolve the surface of the dyed hair.

The permanent hair-waving solution of the present invention contains, as a main ingredient, a reducing agent such as a sulfide, hydrosulfide or thioglycolate of preferably alkali metal or ammonium to cut off the sulfur linking of cystine in the hair, and also contains a sulfite of preferably alkali metal or ammonium in at least equimolar amount to the reducing agent as an acceptor of extra sulfur atom formed in the cutting-off reaction, and further, sucrose, glucose, fructose, or mixtures thereof can be contained as an adjuvant reducing agent in order to prevent the generation of bad smell before or during the application. The reducing agent as the main ingredient can be used in an excess amount only to consume the at least equimolar amount of sulfite in vain, and ordinarily, preferably used in an amount of 0.16–0.4% by weight, more preferably about 0.2% by weight, and the corresponding sulfite is used in an equimolar amount of between 0.14–0.5% by weight, or more, preferably about 0.8% by weight. When the sucrose, glucose, fructose, or mixtures thereof are used, it is preferably used in an amount of up to 0.3% by weight. The aliphatic oxy-organic acid such as citric acid, tartaric acid or the like is contained in an amount of 0.01–0.3% by weight as an oxidation-controlling synergist in the above cutting-off of sulfur linking and for ester formation with the lower aliphatic saturated alcohols when contained and also for maintaining the pH of the permanent hair-waving solution of the present invention at 8 to 11 by the action as a buffer agent. Further, for the purpose of the moisture retention in hair, swelling of hair molecules, polar solvent of hair and ester formation with the above-mentioned oxy-organic acid, lower aliphatic saturated alcohol such as ethyl alcohol, propyl alcohol, glycerin, ethyleneglycol, diethyleneglycol, or mixtures thereof can be contained in an amount of 0.6–10% by weight. Further, organic amines such as monoethanolamine, diethanolamine, triethanolamine, or mixtures thereof can be used as a hair-permeability-promoting agent and deodorizing agent of the main ingredient of used sulfide, hydrosulfide or thioglycolate and also as an air oxidation activator in an amount of 0.01–1.0% by weight, and indispensably, hexamethylenetetramine, iodine, bromine, potassium iodide, sodium iodide, ammonium iodide, potassium bromide, sodium bromide, ammonium bromide, or mixtures thereof must be used as an air oxidation accelerator for accelerating the fixing of hair in an amount of 0.02–1.0% by weight, preferably 0.6% by weight, and pure water is used as the remainder. Thus, a conventionally non-attainable ideal permanent hair-waving solution of the present invention to obtain a truly non-damaged odorless hair after short operation harmlessly can be obtained. In order to more clarify this fact, the following comparative experimental examples are shown. All parts listed are by weight.

COMPARATIVE EXPERIMENTAL EXAMPLES

About 10 untreated human hairs (virgin hairs) well wetted with each test solution were tightly wound on a rod of about 0.45 cm in diameter. After the hairs were allowed to stand at about 30° C. for about 10 minutes (cap time), the hairs as wound on the rod were rinsed with warm pure water at about 40° C. After water attached to the hairs was softly wiped away, the hairs were air-dried by a dryer. The wound hairs were unwound from the rod, further rinsed in warm pure water at 40° C. in a beaker and air-dried on a blotting paper to observe the final diameter, tensile strength and elongation of the curled hair, as shown in the following Table.

TABLE

| Ingredient | One-step solution of U.S. Pat. No. 4,192,863 | Solution according to the present invention Main ingredient | | | | | |
|---|---|---|---|---|---|---|---|
| | | Ammonium thioglycolate | | Sodium sulfide | | Sodium hydrosulfide | |
| Ammonium thioglycolate | 3.2 | 0.2 | 0.2 | — | — | — | — |
| Sodium sulfide | — | — | — | 0.2 | 0.2 | — | — |

TABLE-continued

| Ingredient | One-step solution of U.S. Pat. No. 4,192,863 | Ammonium thioglycolate | | Sodium sulfide | | Sodium hydrosulfide | |
|---|---|---|---|---|---|---|---|
| Sodium hydrosulfide | — | — | — | — | — | 0.2 | 0.2 |
| Sodium sulfite | — | 0.8 | 0.8 | 0.8 | 0.8 | 5.0 | 5.0 |
| Caustic potash | 0.08 | — | — | — | — | — | — |
| Tartaric acid | 0.15 | 0.03 | 0.03 | — | — | 0.22 | 0.22 |
| Citric acid | — | — | — | 0.14 | 0.14 | — | — |
| Ethyl alcohol | 1.00 | 1.0 | 0.6 | 1.0 | 0.6 | 1.0 | 0.6 |
| Glycerin | — | — | 0.4 | — | 0.4 | — | 0.4 |
| 28% Ammonia water | 2.00 | — | — | — | — | — | — |
| Monoethanolamine | 0.03 | 0.03 | 0.03 | 0.03 | 0.03 | 0.03 | 0.03 |
| Potassium iodide | — | 0.6 | — | 0.6 | — | 0.6 | — |
| Hexamethylene- | — | — | 0.6 | — | 0.6 | — | 0.6 |
| Pure Water | 90.34 | 97.34 | 97.34 | 97.23 | 97.23 | 92.95 | 92.95 |
| pH | 9.0 | 9.0 | 8.8 | 9.2 | 9.4 | 9.6 | 9.6 |
| Curled hair diameter (cm) | ca. 1.2 | ca. 1.9 | ca. 2.4 | ca. 2.3 | ca. 2.6 | ca. 1.1 | ca. 1.1 |
| Tensile strength (g) | 128 | 152 | 138 | 146 | 138 | 144 | 149 |
| Elongation (%) | 45.5 | 45.2 | 47.2 | 47.2 | 39.7 | 47.2 | 47.5 |
| Bad smell at the application | Considerably smell | Almost no smell | | Almost no smell | | Almost no smell | |
| Glossiness | Little | Very much | | Very much | | Very much | |
| Flexibility and dampishness | No | Very much | | Very much | | Very much | |

The permanent hair-waving solution of the present invention can be used, for example, in beauty parlors as follows:

(1) The hair is tightly wound in the desired hair style on about 60 rods or curlers having diameters of 0.5 to 1 cm and fastened with rubber bands while optionally coating 30 ml of the permanent hair-waving solution of the present invention. The wound hair is then coated with another 50 ml of the solution.

(2) The head of the user is covered with a vinyl cap for about 10 minutes and then the cap is removed.

(3) The hair as wound is rinsed with warm water, wiped with a towel, and after being allowed to stand for about 15 minutes, the hair is removed from the rod or curler, and then the hair is dried naturally or by a dryer while arranging the hair style to complete the hair waving.

(4) Before the above step (3), if desired, all the hairs or a part of the hairs such as those at the front, crown and nape are taken off the rods or curlers and tightly rewound on curlers having diameters of 1 to 2 cm whereafter hor air is applied to the hairs to produce desired large curls. Even after washing, the large curls retain almost the same diameters as those of the curlers.

Further, as other compounding agents, there can be added perfume, coloring agents and the like.

According to the above processes, it becomes possible to quite easily obtain a substantially odorless, silky, non-porous and non-damaged permanently curled hair having a curl diameter of 2 to 6 cm which is particularly appreciated from a beauty viewpoint even after washing the hair 4 to 6 months later, without the necessity of a setting process, and further quite without possibility of the chemical poisoning with cyano compounds or the like as in the processes using the conventional permanent hair-waving solutions.

The permanent hair-waving solution of the present invention can also be applied to naturally crimped hair to change it into permanently straight hair and also it can be utilized to make silky brilliant hair pieces and wigs or to finish hair waving in making dolls.

The following examples are illustrative of permanent hair-waving solutions of the present invention and which are prepared at room temperature by mixing the constituents with one another. It will be understood that various other solutions may be made following the guiding principles and teachings contained herein, and the examples set forth herein are, therefore, in no way to be regarded as limitative of the full scope of the present invention. All parts listed are by weight.

EXAMPLES 1-3

| Example | 1 | 2 | 3 |
|---|---|---|---|
| Potassium sulfide, sodium sulfide, ammonium sulfide, potassium hydrosulfide, sodium hydrosulfide, ammonium hydrosulfide, potassium thioglycolate, sodium thioglycolate or ammonium thioglycolate | 0.16 | 0.2 | 0.4 |
| Potassium sulfite, sodium sulfite or ammonium sulfite | 0.14-0.5 | 0.8 | 1.0 |
| Citric acid or tartaric acid | 0.01-0.3 | 0.01-0.3 | 0.01-0.3 |
| Hexamethylenetetramine, iodine, bromine, potassium iodide, sodium iodide, ammonium iodide, potassium bromide, sodium bromide, ammonium bromide, or mixtures thereof. | 0.02-1.0 | 0.02-1.0 | 0.02-1.0 |
| Pure water to bring up to 100 parts | | | |
| (pH | 3-11 | 8-11 | 3-11) |

EXAMPLES 4-6

| Example | 4 | 5 | 6 |
|---|---|---|---|
| Potassium sulfide | 0.16 | 0.2 | 0.4 |
| Potassium sulfite, sodium sulfite or ammonium sulfite | 0.14-0.19 | 0.8 | 1.0 |
| Sucrose, glucose, fructose, or mixtures thereof | 0-0.3 | 0-0.3 | 0-0.3 |
| Citric acid or tartaric acid | 0.01-0.3 | 0.01-0.3 | 0.01-0.3 |
| Hexamethylenetetramine, iodine, bromine, potassium | 0.02-1.0 | 0.02-1.0 | 0.02-1.0 |

-continued

| Example | 4 | 5 | 6 |
|---|---|---|---|
| iodide, sodium iodide, ammonium iodide, potassium bromide, sodium bromide, ammonium bromide, or mixtures thereof. | | | |
| Ethyl alcohol, propyl alcohol, glycerin, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 7–9

| Example | 7 | 8 | 9 |
|---|---|---|---|
| Sodium sulfide | 0.16 | 0.2 | 0.4 |
| Potassium sulfite, sodium sulfite or ammonium sulfite | 0.24–0.32 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 10–12

| Example | 10 | 11 | 12 |
|---|---|---|---|
| Ammonium sulfide | 0.16 | 0.2 | 0.4 |
| Potassium sulfite, sodium sulfite or ammonium sulfite | 0.27–0.37 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerine, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 13–15

| Example | 13 | 14 | 15 |
|---|---|---|---|
| Potassium hydrosulfide | 0.16 | 0.2 | 0.4 |
| Potassium sulfite, sodium sulfite or ammonium sulfite | 0.26–0.35 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerine, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 16–18

| Example | 16 | 17 | 18 |
|---|---|---|---|
| Sodium hydrosulfide | 0.16 | 0.2 | 0.4 |
| Potassium sulfite, sodium sulfite or ammonium sulfite | 0.33–0.45 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 19–21

| Example | 19 | 20 | 21 |
|---|---|---|---|
| Ammonium hydrosulfide | 0.16 | 0.2 | 0.4 |
| Potassium sulfite, sodium sulfite or ammonium sulfite | 0.36–0.5 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |

-continued

| Example | 19 | 20 | 21 |
|---|---|---|---|
| (pH | 8–11 | 8–11 | 8–11) |

EXAMPLES 22–24

| Example | 22 | 23 | 24 |
|---|---|---|---|
| Potassium thioglycolate | 0.16 | 0.2 | 0.4 |
| Potassium sulfite, sodium sulfite or ammonium sulfite | 0.14–0.19 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Mono-, di- or tri-ethanolamine, or mixtures thereof | 0.01–1.0 | 0.01–1.0 | 0.01–1.0 |
| Pure water to bring up to 100 parts | | | |
| (pH | 8–11 | 8–11 | 8–11) |

EXAMPLES 25–27

| Example | 25 | 26 | 27 |
|---|---|---|---|
| Sodium thioglycolate | 0.16 | 0.2 | 0.4 |
| Potassium sulfite, sodium sulfite or ammonium sulfite | 0.16–0.22 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Pure water to bring up to 100 parts | | | |
| (pH | 8–11 | 8–11 | 8–11) |

EXAMPLES 28–30

| Example | 28 | 29 | 30 |
|---|---|---|---|
| Ammonium thioglycolate | 0.16 | 0.2 | 0.4 |
| Potassium sulfite, sodium sulfite or ammonium sulfite | 0.17–0.23 | 0.8 | 8.0 |
| Sucrose, glucose, fructose, or mixtures thereof | 0–0.3 | 0–0.3 | 0–0.3 |
| Citric acid or tartaric acid | 0.01–0.3 | 0.01–0.3 | 0.01–0.3 |
| Hexamethylenetetramine, iodine, bromine, potassium iodide, sodium iodide, ammonium iodide, potassium bromide, sodium bromide, ammonium bromide, or mixtures thereof. | 0.02–1.0 | 0.02–1.0 | 0.02–1.0 |
| Ethyl alcohol, propyl alcohol, glycerin, ethyleneglycol, diethyleneglycol, or mixtures thereof | 0.6–10 | 0.6–10 | 0.6–10 |
| Pure water to bring up to 100 parts | | | |
| (pH | 8–11 | 8–11 | 8–11) |

What is claimed is:

1. A one-step, permanent, hair-waving solution, which solution comprises in combination:
   (a) a sulfur-sulfur reducing agent for cystine in an amount sufficient to reduce cystine and to form sulfur and a cysteine salt or cysteine, the agent selected from the group consisting of a sulfide, a hydrosulfide and a thioglycolate;
   (b) a sulfite compound in an amount sufficient to act as an acceptor of the sulfur formed in the reaction of the cystine with the reducing agent and to form a thiosulfate, the molar ratio of sulfite compound to the reducing agent being 1.0 or more;
   (c) an air-oxidation accelerator in an amount sufficient for fixing, by means of accelerated air oxidation, the recovered sulfur-sulfur link of the cystine;
   (d) free alkali in an amount to provide a pH of from about 8 to 11 of the solution; and
   (e) an aqueous carrier for the reducing agent, accelerator, sulfite compound and free alkali.

2. The solution of claim 1 wherein the reducing agent is present as the alkali metal or ammonium salt of the reducing agent.

3. The solution of claim 1 wherein the reducing agent comprises from about 0.16% to 0.4% by weight of the solution.

4. The solution of claim 1 wherein the sulfite compound is present in an amount of from about 0.14% to 0.5% by weight of the solution.

5. The solution of claim 1, which solution is free of a thioglycolate reducing agent.

6. The solution of claim 1 wherein the air-oxidation accelerator is present in an amount of from about 0.01% to 1.0% by weight of the solution.

7. The solution of claim 1 wherein the air-oxidation accelerator is selected from the group consisting of hexamethylenetetramine, iodine, bromine, potassium iodide, sodium iodide, potassium bromide, sodium bromide, ammonium bromide, ammonium iodide and combinations thereof.

8. The solution of claim 1 wherein the sulfite compound is present as the alkali metal or ammonium salt of the sulfite compound.

9. The solution of claim 1 which includes, in an amount up to about 0.3% by weight of the solution, a reductive saccharide selected from the group consisting of sucrose, glucose, fructose and combinations thereof.

10. The solution of claim 1 which includes, in an amount of from about 0.01% to 0.3% by weight of the solution, an aliphatic oxy-organic acid.

11. The solution of claim 10 wherein the aliphatic oxy-organic acid is selected from the group consisting of citric acid, tartaric acid and combinations thereof.

12. The solution of claim 1 which includes from about 0.6% to 10% by weight of the solution of a lower aliphatic saturated alcohol.

13. The solution of claim 12 wherein the saturated alcohol is selected from the group consisting of ethyl alcohol, propyl alcohol, glycerin, ethylene glycol, diethylene glycol and combinations thereof.

14. The solution of claim 1 which includes from about 0.01% to 1.0% by weight of the solution of an organic amine selected from the group consisting of monoethanolamine, diethanolamine, triethanolamine and combinations thereof.

15. A one-step, permanent, hair-waving solution, which solution comprises in combination:
  (a) a sulfur-sulfur reducing agent for cystine, to form a sulfur and a cysteine salt or cysteine, which reducing agent comprises from about 0.16% to 0.4% by weight of the solution and is selected from the group consisting of a sulfide, a hydrosulfide and a thioglycolate, the reducing agent being present as the alkali metal or ammonium salt of the reducing agent;
  (b) an air-oxidation accelerator for fixing, by means of accelerated air oxidation, the recovered sulfur-sulfur link of the cystine, which accelerator is present in an amount of from about 0.01% to 1.0% by weight of the solution and is selected from the group consisting of hexamethylenetetramine, iodine, bromine, potassium iodide, sodium iodide, potassium bromide, sodium bromide, ammonium bromide, ammonium iodide and combinations thereof;
  (c) a sulfite compound as an acceptor of sulfur formed in the reaction of the cystine with the reducing agent to form a thiosulfate, which sulfite compound is present in an amount of from about 0.14% to 0.5% by weight of the solution and is present as the alkali metal or ammonium salt of the sulfite compound, the molar ratio of sulfite compound to the reducing agent being 1.0 or more;
  (d) free alkali to provide a pH of from about 8 to 11 of the solution; and
  (e) an aqueous carrier for the reducing agent, accelerator, sulfite compound and free alkali.

16. The solution of claim 15 which includes, in an amount up to about 0.3% by weight of the solution, a reductive saccharide selected from the group consisting of sucrose, glucose, fructose and combinations thereof.

17. The solution of claim 15, which solution is free of a thioglycolate reducing agent.

18. The solution of claim 15 which includes a saturated alcohol selected from the group consisting of ethyl alcohol, propyl alcohol, glycerin, ethylene glycol, diethylene glycol and combinations thereof.

19. The solution of claim 15 which includes from about 0.01% to 1.0% by weight of the solution of an organic amine selected from the group consisting of monoethanolamine, diethanolamine, triethanolamine and combinations thereof.

20. The solution of claim 15 which comprises in weight percent of the sucrose 0.2%, the hydrosulfide of sodium 0.2%, the sulfite of sodium 0.8%, the citric acid 0.08%, the potassium iodide 0.6%, the ethyl alcohol 0.6% and glycerin 0.4%, the monoethanolamine 0.03% and pure water as the remainder.

21. A process of giving permanent waving shape to hair, which process comprises arranging the hair in a desired style and applying to the hair the permanent hair-waving solution of claim 1 in an amount sufficient to moisten the hair.

22. A process of giving permanent waving shape to hair, which process comprises arranging the hair in a desired style and applying to the hair the permanent hair-waving solution of claim 15 in an amount sufficient to moisten the hair.

* * * * *